US012600818B2

(12) United States Patent
Zedda

(10) Patent No.: US 12,600,818 B2
(45) Date of Patent: Apr. 14, 2026

(54) PROCESS FOR THE PREPARATION OF STERICALLY HINDERED NITROXYL ETHERS

(71) Applicant: GeneusChem AG, Basel (CH)

(72) Inventor: Alessandro Zedda, Muttenz (CH)

(73) Assignee: GeneusChem AG, Basel (CH)

( * ) Notice: Subject to any disclaimer, the term of this patent is extended or adjusted under 35 U.S.C. 154(b) by 0 days.

(21) Appl. No.: 18/853,423

(22) PCT Filed: Mar. 16, 2023

(86) PCT No.: PCT/EP2023/056724
§ 371 (c)(1),
(2) Date: Oct. 2, 2024

(87) PCT Pub. No.: WO2023/194065
PCT Pub. Date: Oct. 12, 2023

(65) Prior Publication Data

US 2025/0223403 A1 Jul. 10, 2025

(30) Foreign Application Priority Data

Apr. 4, 2022 (EP) .................................... 22166462

(51) Int. Cl.
*C08G 73/06* (2006.01)
*C07C 201/12* (2006.01)
*C07D 401/14* (2006.01)

(52) U.S. Cl.
CPC .......... *C08G 73/065* (2013.01); *C07C 201/12* (2013.01); *C07D 401/14* (2013.01)

(58) Field of Classification Search
CPC .... C08G 73/065; C07C 201/12; C07D 401/14
See application file for complete search history.

(56) References Cited

U.S. PATENT DOCUMENTS

| | | | | |
|---|---|---|---|---|
| 4,665,185 | A | 5/1987 | Winter et al. | |
| 5,096,950 | A | 3/1992 | Galbo et al. | |
| 5,130,429 | A | 7/1992 | Piccinelli et al. | |
| 5,204,473 | A | 4/1993 | Winter et al. | |
| 6,177,491 | B1 * | 1/2001 | Galbo | C07D 401/14 544/219 |
| 8,481,726 | B2 | 7/2013 | Basbas et al. | |
| 2005/0014948 | A1 | 1/2005 | Galbo et al. | |
| 2012/0232197 | A1 | 9/2012 | Menozzi et al. | |
| 2017/0107352 | A1 * | 4/2017 | Menozzi | C09K 15/30 |

FOREIGN PATENT DOCUMENTS

| | | | |
|---|---|---|---|
| CN | 108395397 B | | 7/2021 |
| GB | 2334717 A | | 9/1999 |
| WO | WO 2008003602 A1 | | 1/2008 |
| WO | WO 2008003605 A1 | | 1/2008 |
| WO | 2011/029744 A1 | | 3/2011 |
| WO | WO 2012052377 A1 | | 4/2012 |

OTHER PUBLICATIONS

Galbo James P.: "Preparation of tris(1-alkoxy-2,2,6,6-tetramethylpiperidinyl)-1,3,5-triazine-2,4,6-tricarboxylates and analogs as light stabilizers", Jan. 1, 1991 (Jan. 1, 1991), pp. 1-5, Database GNPD [Online] Mintel; XP093326118.

Galbo James P. et al: "N,N',N''-Tris{2,4-bis[(hydrocarbyloxy-2,2,6,6-tetramethylpiperidin-4-yl) alkylamino]-s-triazin-6-yl}-3,3'ethylenediiminodipropylamines, their isomers and bridged derivatives, preparation thereof, and organic compositions stabilized therewith", Jan. 1, 1998 (Jan. 1, 1998), pp. 1-5, Database GNPD [Online] Mintel; XP093326121.

Yamamoto Sanehiro: "Polyolefin compositions for agricultural films with long-lasting weather resistance and excellent heat resistance", Jan. 1, 2003 (Jan. 1, 2003), pp. 1-3, Database GNPD [Online] Mintel; XP093326123.

Basbas Abdel-Ilah et al: "Process for the preparation of sterically hindered nitroxyl ethers", Jan. 1, 2008 (Jan. 1, 2008), pp. 1-5, Database Gnpd [Online] Mintel; XP093326126.

Costa Joao et al: "A flame-retardant composition based on polyamides", Jan. 1, 2020 (Jan. 1, 2020), pp. 1-4, Database GNPD [Online] Mintel; XP093326140.

* cited by examiner

*Primary Examiner* — Shane Fang
(74) *Attorney, Agent, or Firm* — Leydig, Voit & Mayer, Ltd.

(57) ABSTRACT

Provided is a process for alkylating a sterically hindered nitroxyl compound to the corresponding sterically hindered alkoxyamine, which process comprises reacting said sterically hindered nitroxyl compound with a peroxide selected from diacyl peroxides of the formula (A), peresters of the formula (A) and oxalic acid peresters of the formula (D)

R—CO—O—O—Z—R (A),

R—Z''—X—CO—CO—O—O—Z''—R (D), wherein each R independently stands for a primary or secondary alkyl or cycloalkyl radical, and
X is oxygen —O— or a peroxy group —O—O—,
Z stands for CO or an alkylene bonded over a quaternary carbon atom, which is an alkylene of the formula (C)

R'—C—R' (C)

wherein each R' is selected from alkyl of 1 to 15 carbon atoms,
Z'' stands for said alkylene bonded over a quaternary carbon atom of the formula (C),
provided that, in case that Z is CO, the sterically hindered nitroxyl compound is not 4-hydroxy-1-oxyl-2,2,6,6-tetramethyl-piperidine, and other processes and products.

19 Claims, No Drawings

PROCESS FOR THE PREPARATION OF STERICALLY HINDERED NITROXYL ETHERS

CROSS-REFERENCE TO PRIOR APPLICATIONS

This application is a U.S. National Phase application under 35 U.S.C. § 371 of International Application No. PCT/EP2023/056724, filed on Mar. 16, 2023, and claims benefit to European Patent Application No. EP 22166462.6, filed on Apr. 4, 2022. The International Application was published in English on Oct. 12, 2023 as WO 2023/194065 A1 under PCT Article 21(2).

FIELD

The present invention relates to a novel process for the alkylation of certain N-oxyl secondary amines and to the preparation of corresponding N-alkoxyamines in high purity. More specifically in one embodiment, the new chemical process pertains to the preparation of such sterically hindered N-alkoxyamines by selective O-alkylation of nitroxyls by reaction with certain primary or secondary alkyl radicals; the process may further comprise a prior oxidation step to obtain said sterically hindered nitroxyl from the corresponding secondary (N—H) amine.

Further described are some novel compounds obtainable with the present process. The products of present process may be used in various fields of chemistry and polymer technology; an important class of products belong to the sterically hindered amines, which are commonly used in polymer technology, for example, as flame retardants, polymerization regulators, or as stabilizers for organic material, such as organic polymer compositions, against degradation by light, oxygen and/or heat.

BACKGROUND

A number of publications describe the stabilization of organic material using specific sterically hindered amine compounds as stabilizers, such compounds are also known as hindered amine light stabilizers (HALS). A valuable class of sterically hindered amines are compounds wherein the nitrogen atom bonds to 2 tertiary carbon atoms, which are part of two hydrocarbon residues or are part of one heterocyclic ring such as a piperidine ring. For use as stabilizers, such compounds may contain unsubstituted nitrogen (NH—HALS), or substituted nitrogen (e.g. N— alkyl HALS); an important class, due to specific properties such as the reduced basicity of these compounds, are HALS compounds whose hindered nitrogen atom carries an additional organic substituent linked over an oxygen atom (typically N—O-alkyl HALS, see e.g. U.S. Pat. Nos. 5,204,473, 5,096,950); such N—O-alkyl HALS compounds are also referred to as hindered amine ethers. Further applications of sterically hindered amines, especially N—O-alkyl HALS, include uses as flame retardants, rheology modifiers, free radical initiators for controlled polymerization (see Nitroxyl radicals and nitroxyl ethers beyond stabilization: radical generators for efficient polymer modification, Rudolf Pfaendner, C. R. Chimie 9 (2006) 1338-1344).

Most of the commercial applications of hindered N-Alkoxyamines require a well-defined thermal stability of the product. As it is well known in the scientific literature, the Carbon-Oxygen bond of the hindered N-Alkoxyamines has a low bond energy while properties like thermal stability or dissociation are dictated by such bond strength. As described in above references, the thermal degradation of certain N-Alkoxyamines (especially N—O-alkyl HALS) for use as flame retardants or in rheology modifiers applications, is designed to occur at the desired temperatures. Typically, at the extrusion temperature, to trigger free radical reactions between the N-Alkoxyamines and the molten polymer. This leads to polymer chain scission or crosslinking, which modify both the rheology of the molten polymer and the mechanical properties of the resulting final plastic article. For such applications, the R groups of N-Alkoxyamines in flame retardants and rheology modifers are selected with an R substituent with a lower thermal stability compared to light stabilizers. Typically for light stabilization applications, in contrast, the N-Alkoxy derivatives are designed with the highest thermal stability possible to avoid any changes in rheology or mechanical properties of the plastic article.

Due to the above reasons, for the manufacturing of products based on hindered N-Alkoxyamines with well-defined thermal stability, it is very desirable to use a versatile process, applicable to a broad range of hindered N-Alkoxyamines with a range of different R substituents, and capable of high yields and high selectivity in the desired N-Alkoxyamine. In fact, many known manufacturing processes of N-Alkoxyamines have low selectivities towards the desired product, leading to the formation of undesired by-products, with thermal stability or activation temperature outside of the desired temperature range. This is even more important in the case of molecules with multiple hindered amine moieties, like the precursors of oligomeric HALS stabilizers, flame retardant or rheology modifiers, where such by-products cannot be separated by purification and become part of the final products, with potential negative effect on its thermal stability and color of the product. The preparation of sterically hindered nitroxyl compounds is described e.g. in U.S. Pat. No. 4,665,185; a recent evaluation of methods relating to oligomeric compounds and converting the red nitroxyls into the high molecular weight N—O—alkyl HALS is given by E. Cote et al. (Org. Process Res. Dev. 2014, 18, 12, 1843-1849 (https://doi.org/10.1021/op500301r)).

It is also desirable to use manufacturing process with high productivity, low cost and based on the principle of Green Chemistry, especially free of heavy metals.

The secondary amine or hindered amine precursors are largely commercially available or can be prepared by the application of known methods. These secondary hindered amines, which are characterized by their N—H moiety, are conveniently converted into the corresponding nitroxyls by methods described in the literature. Useful precursors can be found, inter alia, in the above references and documents cited therein, see e.g. WO-2008-003605 page 12 line 22 to page 13 line 5.

A problem arising in known conversions of appropriate precursors such as HALS with NH- or N-oxyl functionalities into the corresponding sterically hindered amine alkyl ethers is often an unsatisfactory conversion rate or percentage of unreacted precursor functionalities in the product, which may be detrimental e.g. for its thermal stability or cause undesired side reactions. For example, the N-methoxy hindered amine obtained after thermolysis of a chlorobenzene solution of nitroxyl radical and di-tert-butyl peroxide (example 1 of U.S. Pat. No. 5,204,473) requires a purification step via chromatography to isolate the desired product from the by-products and unreacted starting material.

Conversion of the N-oxyl precursors into the corresponding sterically hindered amine alkyl ethers still may be improved with regard to efficiency and environmental aspects.

SUMMARY

In an exemplary embodiment, the present invention provides a process for alkylating a sterically hindered nitroxyl compound to the corresponding sterically hindered alkoxyamine. The process includes reacting the sterically hindered nitroxyl compound with a peroxide selected from diacyl peroxides of the formula (A), peresters of the formula (A) and oxalic acid peresters of the formula (D)

R—CO—O—O—Z—R (A),

R—Z"—X—CO—CO—O—O—Z"—R (D), wherein each R independently stands for a primary or secondary alkyl or cycloalkyl radical, and X is oxygen —O— or a peroxy group —O—O—, Z stands for CO or an alkylene bonded over a quaternary carbon atom, which is an alkylene of the formula (C)

R'—C—R' (C)

wherein each R' is selected from alkyl of 1 to 15 carbon atoms, Z" stands for said alkylene bonded over a quaternary carbon atom of the formula (C), provided that, in case that Z is CO, the sterically hindered nitroxyl compound is not 4-hydroxy-1-oxyl-2,2,6,6-tetramethyl-piperidine.

DETAILED DESCRIPTION

In an embodiment, the present invention relates to a novel process for the alkylation of sterically hindered nitroxyl radicals and the preparation of corresponding sterically hindered nitroxyl ethers. More specifically, the new chemical process pertains to the preparation of sterically hindered nitroxyl ethers by highly selective O-alkylation via generation and coupling of carbon centered radicals starting from an appropriate precursor from the class of free radical initiators or photoinitiators under specific reaction conditions. Short reaction times, high selectivity and high yields of the desired nitroxyl ethers are a very important feature of the novel process, especially for the preparation of compounds containing a multitude of hindered amine ether functionalities such as polymeric compounds, due to the high conversion rate of the N-oxyl moieties in oligomeric or macromolecular HALS. The products of the present process are of high commercial importance as stabilizers, flame retardants, rheology modifiers, or initiators for controlled polymerization.

It thus has been found that nitroxyl compounds, such as sterically hindered nitroxyls described in the literature inter alia as precursor for the preparation of radical scavenging additives like N—O-alkyl HALS, may be alkylated on the oxygen atom to obtain the corresponding sterically hindered alkoxyamine, by reaction with a peroxide.

The peroxide is selected from diacyl peroxides of the formula (A), peresters of the formula (A) and oxalic acid peresters of the formula (D)

R—CO—O—O—Z—R (A),

R—Z"—X—CO—CO—O—O—Z"—R (D), wherein each R independently stands for a primary or secondary alkyl or cycloalkyl radical, the primary or secondary alkyl or cycloalkyl radical preferably comprising 1 to 15 carbon atoms, and X is oxygen —O— or a peroxy group —O—O—, Z stands for CO or an alkylene bonded over a quaternary carbon atom, which is an alkylene of the formula (C)

R'—C—R' (C)

wherein each R' is selected from alkyl of 1 to 15 carbon atoms,

Z" stands for said alkylene bonded over a quaternary carbon atom of the formula (C).

In case that Z is CO, the sterically hindered nitroxyl compound is not 4-hydroxy-1-oxyl-2,2,6,6-tetramethyl-piperidine.

The peroxide for use in the present process often is a di-acylperoxide of the formula (B)

R—CO—O—O—CO—R (B)

wherein each R independently stands for a primary or secondary alkyl or cycloalkyl radical, the primary or secondary alkyl or cycloalkyl radical preferably comprising 1 to 15 carbon atoms.

Summarizing an embodiment of the present invention, it thus has been found that nitroxyl compounds, such as sterically hindered nitroxyls described in the literature inter alia as precursor for the preparation of radical scavenging additives like N—O-alkyl HALS, may be alkylated on the oxygen atom to obtain the corresponding sterically hindered alkoxyamine, by reaction with a peroxide of the formula (A)

R—CO—O—O—Z—R (A), or preferably a di-acylperoxide of the formula (B)

R—CO—O—O—CO—R (B)

wherein Z stands for CO or an alkylene bonded over a quaternary carbon atom, i.e. an alkylene of the formula (C)

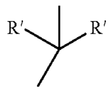

(C)

wherein each R' is selected from alkyl of 1 to 15 carbon atoms, and each R independently stands for a primary or secondary alkyl or cycloalkyl radical, the primary or secondary alkyl or cycloalkyl radical preferably comprising 1 to 15 carbon atoms.

The peroxide may also be selected from oxalic acid peresters of the formula (D)

R—Z"—X—CO—CO—O—O—Z"—R (D), wherein each R independently stands for a primary or secondary alkyl or cycloalkyl radical, the primary or secondary alkyl or cycloalkyl radical preferably comprising 1 to 15 carbon atoms, and X is oxygen —O— or, preferably, a peroxy group —O—O—;

and Z" stands for alkylene bonded over a quaternary carbon atom of the formula (C)

R'—C—R' (C)

wherein each R' is selected from alkyl of 1 to 15 carbon atoms,

Such peroxides based on oxalic acid may bring about the advantage of milder reaction conditions, such as reduced reaction temperature as noted further below.

It has been found that, surprisingly, this reaction leads to the corresponding O— alkylated derivative, preferably N—O-alkyl HALS, with extremely high selectivity and conversion rate, and without requirement to use catalysts, especially metal or iodide catalysts.

High selectivity and conversion rate are factors in case of oligomeric or polymeric products for improving the product quality. Such N-alkoxy compounds with high thermal stability are also suitable as stabilizers for polymers with higher extrusion temperature, for example polypropylene fibers and non-wovens, since they will survive the processing without changing properties of the polymer while still providing the undiminished stabilization performance.

Due to its high conversion rate, the present process is also suitable for improving the product quality of N—O-alkyl HALS products, some of which are commercial, which may be impaired by their content of unreacted nitroxyl and/or an undesired coloration of the product.

In an embodiment, the invention further pertains to a process as described above for the conversion of a sterically hindered nitroxyl compound, characterized by comprising one or more groups of the formula (IIIa)

(IIIa)

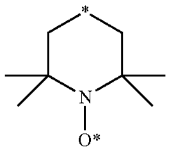

into the corresponding N—O-alkyl compound, wherein the educt already is partly converted and already comprises one or more groups of the formula (Ia)

(Ia)

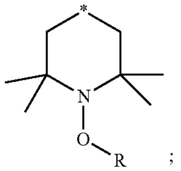

the asterisk in each formula indicating the location of the bond linking these moieties to another part of the molecule, while R denotes the alkyl group defined above.

Such process for improving the product quality and alkylation rate is, consequently, especially useful in the case of oligomeric or polymeric compounds comprising at least 6, for example 6 to 100, moieties if the formula (Ia), while also containing some unreacted nitroxyl moieties, e.g. of the formula (Ilia). Typical products of these classes are shown further below.

It is another finding of an embodiment of the present invention, that nitroxyl compounds such as sterically hindered nitroxyls may be converted in the absence of metal catalysts (also denoted as heavy metals), or even any catalytic agent, to the corresponding alkoxyamines, following the process presently described.

Within the scope of present invention, the term "primary alkyl" or "secondary alkyl or cycloalkyl" radical denotes any alkyl or cycloalkyl group forming a carbon centered radical, whose radical center bonds to another carbon and 2 hydrogen atoms or to 3 hydrogen atoms, thus forming a primary carbon radical or a methyl radical as a specific form thereof; or the radical center bonds to 2 carbon atoms and 1 hydrogen atom, thus forming a secondary carbon radical. The term "radical" stands for a monovalent group (i.e. primary alkyl group or secondary alkyl or cycloalkyl group) when part of a molecule, like in abovesaid educt and product of the process (i.e. the di-acylperoxide and the alkoxyamine). The primary or secondary carbon of present moiety R is not part of a conjugated system (like benzylic or allylic or cyano); it is preferably not adjacent to an electro-withdrawing group, otherwise the thermal stability would be reduced.

In a preferred process of an embodiment of the invention, R is independently selected from methyl, ethyl, 1-propyl, 2-propyl, 1-butyl, 2-butyl, 1-pentyl, 2-pentyl, 3-pentyl, 1-hexyl, 2-hexyl, 3-hexyl, 1-heptyl, 2-heptyl, 3-heptyl, 4-heptyl, 1-octyl, 2-octyl, 3-octyl, 4-octyl, nonyl, decyl, undecyl, dodecyl, cyclopentyl, cyclohexyl, cycloheptyl, cyclooctyl, cyclononyl, cyclodecyl, cycloundecyl, cyclododecyl; especially wherein both residues R stand for the same radical.

The term "sterically hindered amine" denotes a secondary or tertiary amine whose nitrogen atom bonds to 2 carbon atoms, each thereof being quaternary carbon.

The term "metal catalysts" typically includes transition metals such as copper, iron, palladium; generally, it stands for any compound comprising a metal element other than alkaline or alkaline earth elements.

The term "alkylate" or "alkylation" denotes the reaction proceeding in the process of an embodiment of the invention, comprising the formation of a chemical bond between alkyl group such as R and the oxygen of the nitroxyl radical.

In a typical process of an embodiment of the invention, the sterically hindered alkoxyamine obtained is a compound of the formula (I)

$$(R_2)_2N—OR \quad (I)$$

wherein R is as defined in claim 1 or 2 or 3;

each $R_2$ is a hydrocarbon, and preferably interlinked to form one divalent hydrocarbon residue, both $R_2$ together containing 2 to 500 carbon atoms, and optionally further containing one or more moieties selected from the group consisting of tertiary nitrogen moieties, secondary nitrogen moieties; ester moieties COO; chloro.

R is preferably alkyl selected from $C_1$-$C_{12}$alkyl or $C_5$-$C_8$cycloalkyl; and each $R_2$ is a hydrocarbon, and preferably interlinked to form one divalent hydrocarbon residue, both $R_2$ together containing 2 to 500 carbon atoms and optionally one or more tertiary nitrogen moieties, one or more ester moieties COO, and/or one or more divalent moieties >N—OR.

The sterically hindered nitroxyl educt typically belongs to the class of 1-oxyl-2,2,6,6-tetramethyl-piperidines containing one or more moieties of the formula (IIIa), and the corresponding sterically hindered alkoxyamine compound belongs to the class of 1-alkoxy-2,2,6,6-tetramethyl-piperidines containing one or more moieties of the formula (Ia), wherein the asterisk indicates the location of the bond linking these moieties to another part of the molecule (Ia)

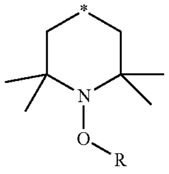

(IIIa)

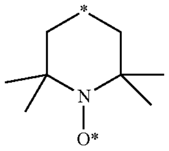

and R is as defined above.

The sterically hindered alkoxyamine compound obtainable in present process often conforms to the formula (Ib)

$$(HA)_pY \quad \text{(Ib)}$$

wherein

HA is a hindered amine ether moiety (HE) of the formula (Ia) as defined above;

p is a number from the range 1 to 6, and wherein

Y is hydrogen, oxo, or Y is an anchor group of valency 2 to 6 of the formula (IX)

$$T_3\text{-}(N[T_4]\text{-}A_2)_q\text{-}N[T_1T_2] \quad \text{(IX)}$$

wherein q ranges from 0 to 3, or Y is an anchor group as further defined below;

when p is 1,

Y is an anchor group of the formula -DC-$A_1$;

when p is 2, Y is an anchor group of the formula DC-$A_2$-DC;

or Y is said divalent anchor group of the formula (IX), wherein q is zero, $T_3$ stands for an open bond, $T_1$ is as defined for $R_1$ and $T_2$ is a divalent aminotriazinyl of the formula (X)

(X)

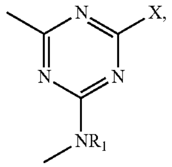

or q is 1, each of $T_1$ and $T_3$ is as defined for $R_1$ and each of $T_2$ and $T_4$ is said divalent aminotriazinyl of the formula (X);

when p is 3, Y is a trivalent anchor group of the formula (IX), wherein q is zero, $T_3$ stands for an open bond, $T_1$ is as defined for $R_1$ and $T_2$ is a trivalent diaminotriazinyl of the formula (XI)

(XI)

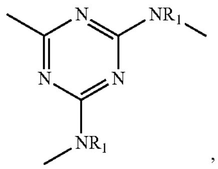

, or q is 1, $T_1$ is as defined for $R_1$, $T_2$ is a divalent aminotriazinyl of the formula (X), and $T_3$ and $T_4$ independently stand for an open bond or a divalent aminotriazinyl of the formula (X);

when p is 4, Y is a tetravalent anchor group of the formula (IX), wherein q is 3 and $T_2$ and two of the residues $T_4$ stand for a divalent diaminotriazinyl of the formula (XI), while each $T_1$ and $T_3$ and the remaining residue $T_4$ are as defined for $R_1$;

when p is 5, Y is a pentavalent anchor group of the formula (IX), wherein q is 1, $T_1$ is a trivalent diaminotriazinyl of the formula (XI), $T_3$ is a divalent aminotriazinyl of the formula (X), and $T_2$ and $T_4$ independently stand for an open bond or a divalent aminotriazinyl of the formula (X);

when p is 6, Y is a hexavalent anchor group of the formula (IX), wherein q is 1, each of $T_1$ and $T_3$ is a trivalent diaminotriazinyl of the formula (XI), and $T_2$ and $T_4$ independently stand for an open bond or a divalent aminotriazinyl of the formula (X);

or q is 2 and $T_2$ and each $T_4$ stand for a trivalent diaminotriazinyl of the formula (XI), while each $T_1$ and $T_3$ is as defined for $R_1$;

or q is 3 and $T_2$ and two of the residues $T_4$ stand for a trivalent diaminotriazinyl of the formula (XI), while each $T_1$ and $T_3$ and the remaining residue $T_4$ are as defined for $R_1$;

or q is 3 and $T_2$ and $T_3$ and one of the residues $T_4$ stand for a trivalent diaminotriazinyl of the formula (XI), while each $T_1$ and the remaining residue $T_4$ are as defined for $R_1$;

$A_1$ is $C_1$-$C_{12}$alkyl or $C_2$-$C_{12}$alkyl interrupted by O or COO; or is di(dialkylamino)triazinyl whose alkyl groups are selected from $C_1$-$C_{12}$alkyl and preferably are identical;

$A_2$ is $C_2$-$C_{12}$alkylene;

DC is a divalent connecting moiety, typically a direct bond, an ester moiety —COO—, ether moiety —O—, or amino moiety of the formula —$NR_1$—; and $R_1$ is H or lower alkyl, especially H or $C_1$-$C_6$alkyl; and X is Cl or $N(R_1)_2$.

The number of open bonds in the anchor group Y equals p.

Each of the moieties of formulae (X) and (XI) contain two different classes of open bonds, one at the triazine core and one (formula (X)) or two (formula (XI)) at $NR_1$. When present in the anchor group of the formula (IX), the one open bond from the triazine core always bonds to the nitrogen atom in formula (IX). Consequently, the open bonds at $NR_1$ bond to the moiety of formula (Ia) or (IIIa).

Examples for preferred products obtainable in embodiments of the present process are compounds of the formula (Ib) wherein Y is an anchor group of the formula (IX), wherein q is from the range 0 to 3;

each of $T_1$, $T_2$, $T_3$ and, if present, $T_4$, is as defined for $R_1$ or is an open bond or is diaminotriazinyl of the formula (XII)

(XII)

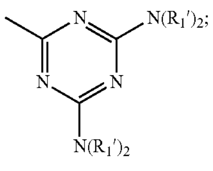

and in case that p is 4 or 6, also Y comprises a tetravalent or hexavalent moiety of the formula (XIII)

(XIII)

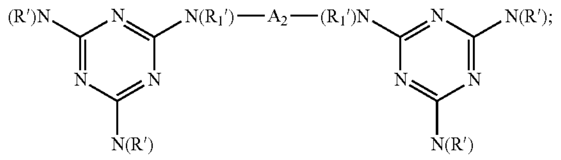

wherein each of R' and $R'_1$ is as defined for $R_1$ or is an open bond, provided that the number of open bonds in the anchor group Y equals p.

An example is a compound comprising an anchor group of the formula (XIII) wherein $A_2$ is tetra-, penta- or hexamethylene, each $R'_1$ is an open bond, each of R' is $C_2$-$C_6$ alkyl, especially butyl; the anchor group thus providing 6 open bonds, one on each aliphatic nitrogen atom. The term “aliphatic” is herein understood as not belonging to a ring structure comprising double bonds. All 6 open bonds thus are linked to a hindered amine moiety of the formula (Ia).

Consequently, the sterically hindered nitroxyl educt typically conforms to the formula (Ic)

$$(HOx)_pY \quad \text{(Ic)}$$

wherein

HOx is a hindered amine oxyl moiety of the formula (IIIa) as defined above;

and p and Y are as defined for formula (Ib) above.

The reaction is typically carried out for a period of 5 minutes to 100 hours. The reaction is typically carried out in the absence of a heavy metal catalyst.

The invention further pertains in an embodiment to a process for converting a sterically hindered secondary amine (i.e. an N—H amine as educt) into the corresponding alkoxylated amine (i.e. N—O-alkyl amine, preferably N—O-alkyl HALS) by i) contacting the secondary hindered amine with a suitable oxidant to obtain a nitroxide (NO—); and subsequently ii) reacting the product obtained in step (i) with with a peroxide of the formula (A) or preferably (B) in accordance with the method described above.

Each of the above steps, i.e. step (i) oxidizing the secondary amine to the oxyl, and step (ii) of an embodiment of the present invention converting said nitroxyl into the corresponding alkoxyamine, is typically carried out in the liquid phase and at a temperature from the range 0 to 140° C., e.g. 0 to 120° C., especially in the presence of an inert solvent.

Methods for carrying out present step (i), and oxidants used for this step, are generally known in the art (see e.g. documents cited above). Oxidants are typically peroxides like hydrogen peroxide,hydrogen peroxide releasing compounds, peracids (e.g. peracetic acid).

Preferred temperatures, especially for present step (ii), are from the range 15 to 100° C., especially 30 to 100° C., most preferably in case that the peroxide used in present process is a diacyl peroxide (formula A) or oxalic acid perester (formula D).

Present process, including step (i) and step (ii), is preferably carried out in the presence of a solvent, which is selected from non-polar solvents like C5-C12 hydrocarbons, for example alkanes, cycloalkanes, aromatic hydrocarbons or arylalkanes, optionally dried; and polar solvents like alcohols, ethers, esters, especially comprising methyl and/or tert.-alkyl moieties, for example tert.butanol, methyl-tert-.butyl ether, methyl acetate, tert.butyl acetate. Of special technical importance are mixtures of such non-polar and polar solvents. Of specific technical interest is a process, wherein the reaction is carried out under a protective gas excluding oxygen, for example under nitrogen.

Of industrial importance is a process for alkylating a sterically hindered nitroxyl compound to the corresponding sterically hindered alkoxyamine, which process comprises reacting said sterically hindered nitroxyl compound with a peroxide of the formula (A) or especially formula (B) as described above, and wherein the sterically hindered nitroxyl compound conforms to the formula

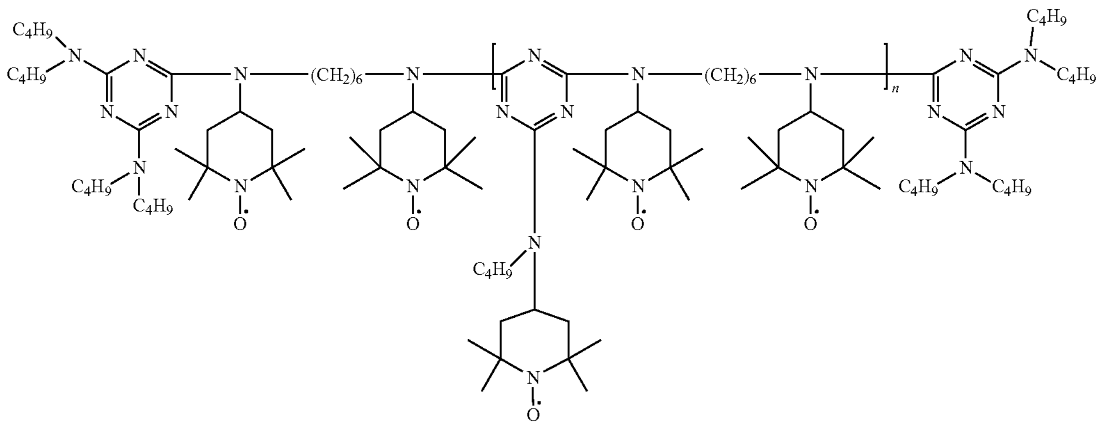

and the sterically hindered alkoxyamine conforms to the formula (V)

(V)

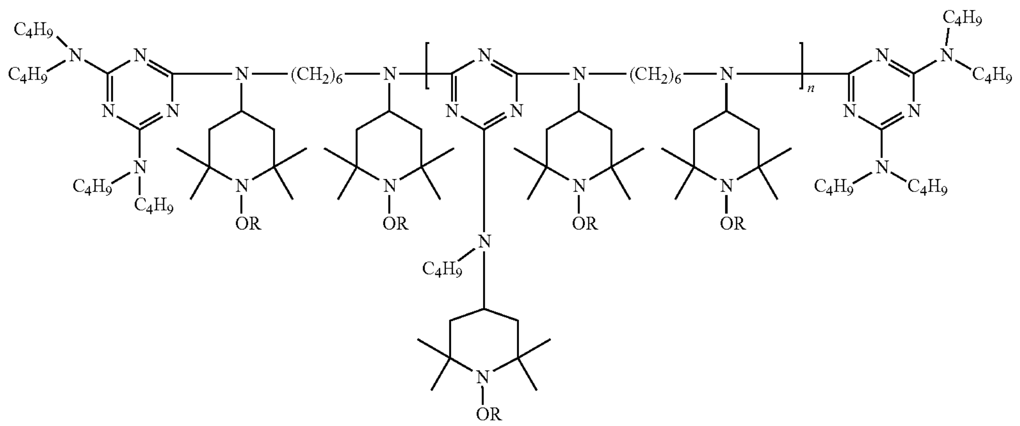

wherein n in each formula ranges from 1 to 10 and R is as defined in claim 1 or 2, and preferably is C1-C5alkyl, especially 1-propyl.

Likewise important is a process wherein, in a first step (i), the sterically hindered secondary amine educt of the formula

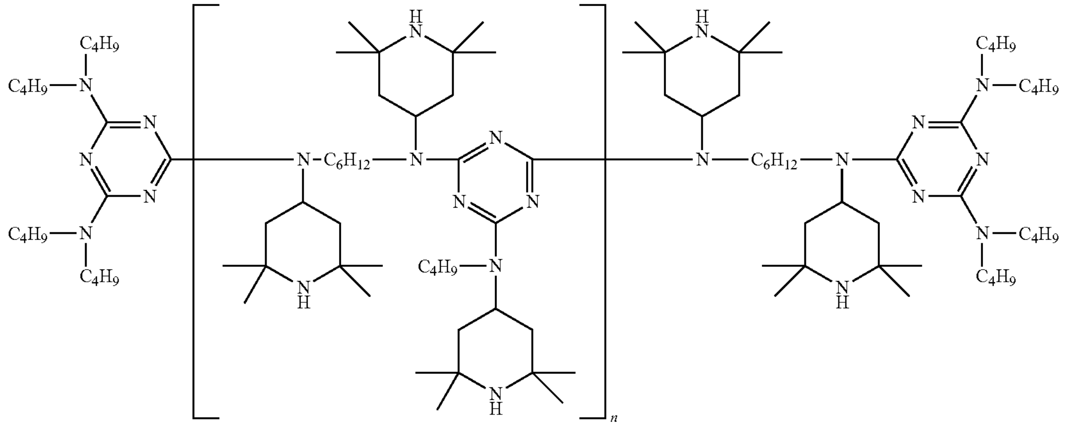

where n is as defined above for formula (V), is converted into said sterically hindered nitroxyl compound, said process comprising i) contacting said secondary hindered amine educt with a suitable oxidant to obtain said nitroxide (NO—) compound; and subsequently ii) reacting the product obtained in step (i) with with a peroxide of the formula (A) or preferably (B) to obtain abovesaid compound of the formula (V).

Due to the high conversion rate achieved in the present process, the conversion of large molecules comprising a multitude of nitroxyl groups, e.g. 6 or more, leads to a N—O-alkyl product which is substantially different from the produnts obtained with conventional alkylations. The invention thus further pertains in another embodiment to an oligomeric or polymeric product comprising compounds containing at least 6, for example 6 to 100, especially 8 to 100, moieties of the formula (Ia), wherein the asterisk indicates the location of the bond linking these moieties to another part of the molecule, (Ia)

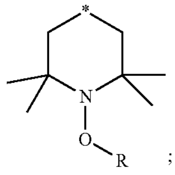

;

as obtainable in the present process. The novel product is preferably an oligomeric or polymeric sterically hindered alkoxyamine compound corresponding to one of the formulae (IV) or (V)

(IV)

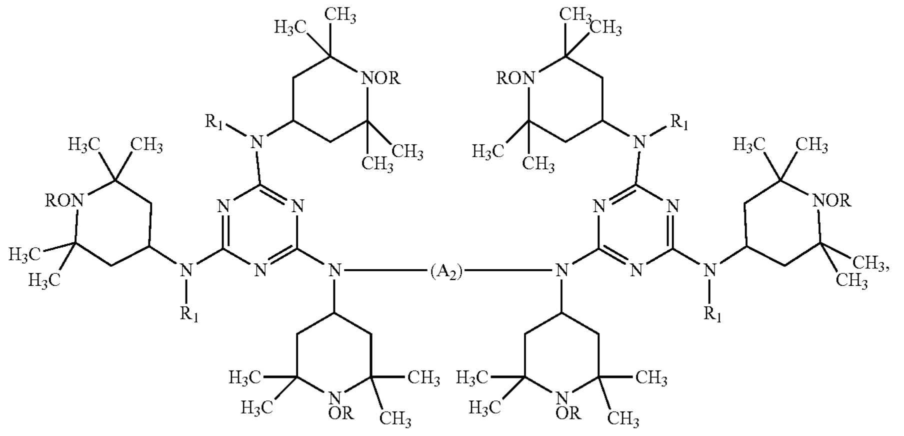

wherein $A_2$, and $R_1$ are as defined in previous claims and R is as defined below for formula (V), (V)

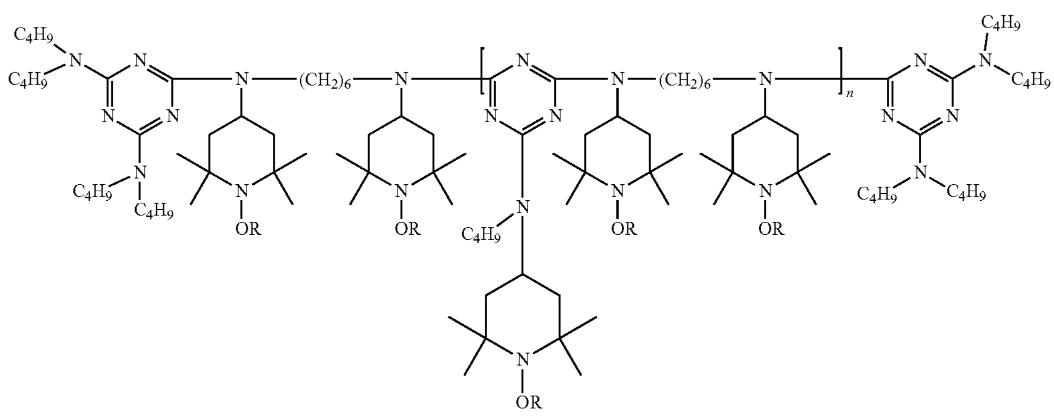

wherein n ranges from 1 to 10 and R is as defined in claim 1 or 3, and preferably is $C_1$-$C_5$alkyl, especially 1-propyl;

characterized in that said oligomeric or polymeric product is obtainable by the process according to present disclosure.

As noted above, prior art conversions of oligomeric or polymeric HALS into N—O— alkyl typically lead to products containing certain amounts of unreacted nitroxyl, and potentially further moieties remaining unreacted resulting from side reactions. In consequence of the high conversion rate of nitroxyls according to the present process to alkoxyamine in the product, an embodiment of the present invention provides a novel product comprising one or more compounds represented by abovesaid formula (V), which is characterized in that it contains more than 87%, preferably 90 to 99.9%, more preferably more than 95%, typically 96% to 99.9%, of educt nitroxyls converted into alkoxyamine moieties N—OR as shown in formula (V), especially wherein R is 1-propyl. The product thus comprises a mixture of compounds, wherein compounds alike those of formula (V) are contained, but with one or more moieties N—OR replaced by nitroxyl, typically also other derivatives of tetramethylpiperidine moiety such as N—H, hydroxylamine or lower alkylamine, which corresponds to unreacted material or moieties, or products of side reactions. Present invention in an embodiment thus allows for an enormous reduction of nitroxyls remaining in the end product, e.g. to 0.1 to 4% of nitroxyls initially present in the educt.

Preferred secondary amine educts for present step (i) include the following compounds:

Educt 1 of the formula:

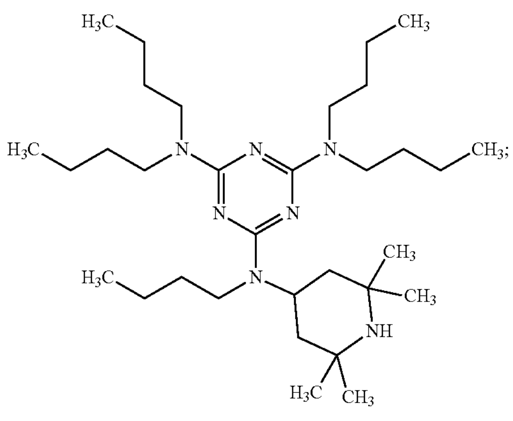 [SMILES: CCCCN(CCCC)c1nc(N(CCCC)CCCC)nc(N(CCCC)C2CC(C)(C)NC(C)(C)C2)n1]

Educt 2 of the formula:

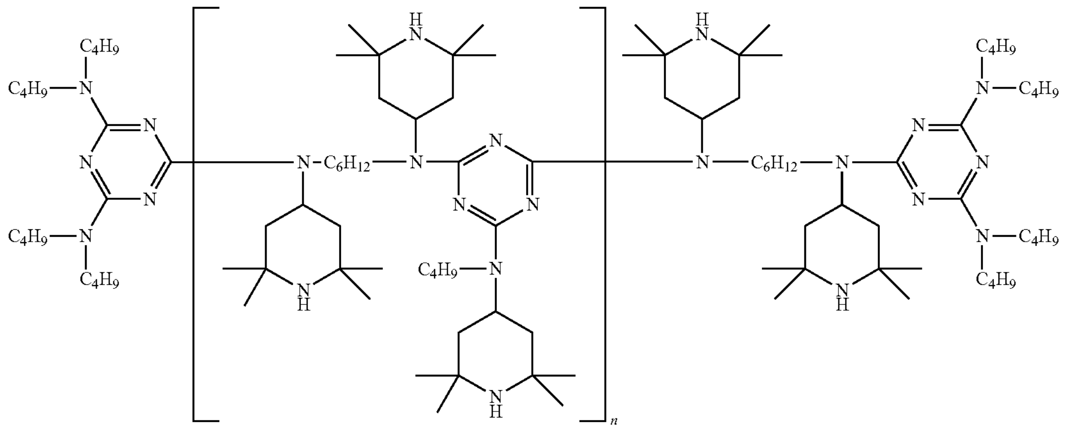

wherein n ranges from 1 to 10 (available as Chimassorb 2020 ® from BASF);

Educt 3 of the formula:

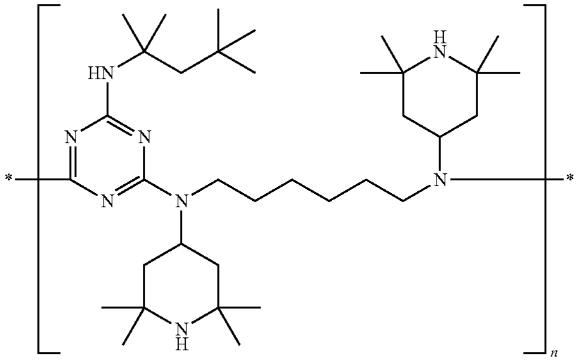

wherein n ranges from 1 to 10, especially 4 to 5 (available as Chimassorb 944 ® from BASF);

Educt 4 of the formula:

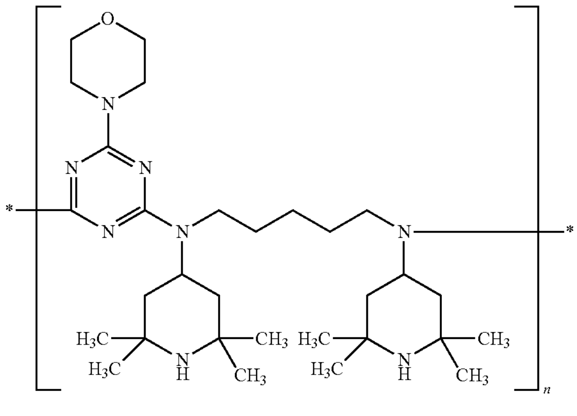

which is available as Cyasorb UV-3346 (®; CAS-No. 90751-07-8) from Solvay;

Educt 5 of the formula:

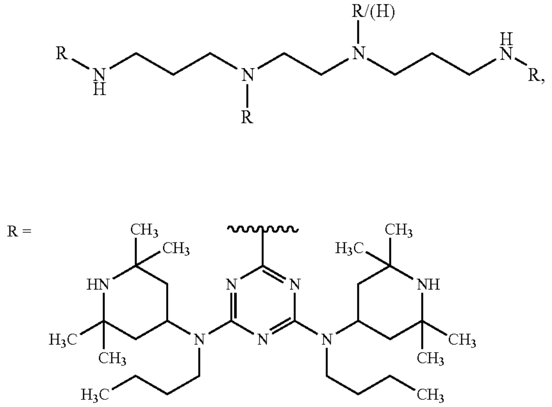

which has been described as educt for example 11 in U.S. Pat. No. 5,130,429 (related to Chimassorb 119 ®, BASF); the analogous structure (with 3 instead of 4 R groups in the tetramine), in form of the N-cyclohexyloxy derivative is available as Flamestab NOR 116 ® from BASF;

Educt 6 of the formula:

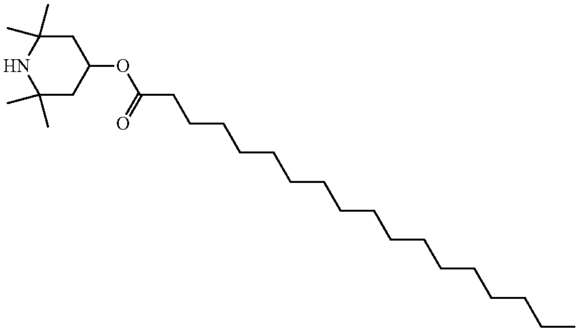 [SMILES: CCCCCCCCCCCCCCCCCC(=O)OC1CC(C)(C)NC(C)(C)C1]

which is available as Cyasorb 3853 (®; CAS-No. 24860-22-8);

Educt 7 of the formula:

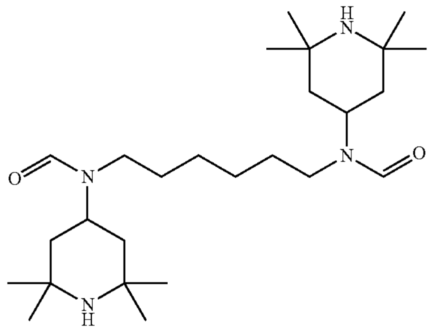

which is available as Uvinul 4050 (®; CAS-No. 123172-53-8);

Educt 8 of the formula:

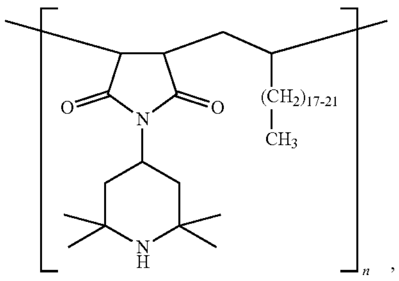

which is available as Uvinul 5050 (®; CAS-No. 199237-39-3);

Educt 9 of the formula:

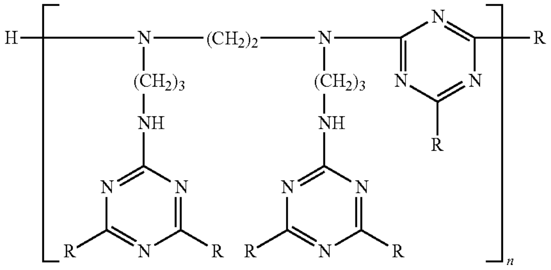

wherein R represents a moiety of the formula

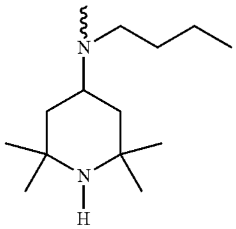

wherein the wiggled line denotes the bond to the molecule shown above (Uvasorb HA 88 ®; CAS-No. 136504-96-6), available from 3V Sigma;

Educt 10 of the formula:

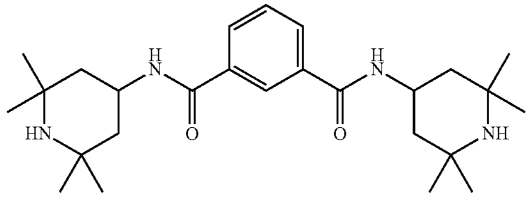

which is available as Nylostab S-EED (®; CAS-No. 42774-15-2) from Clariant;

Educt 11 of the formula:

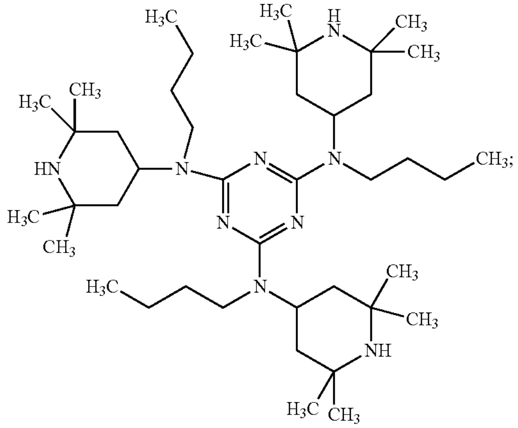 [SMILES: CCCCN(c1nc(N(CCCC)C2CC(C)(C)NC(C)(C)C2)nc(N(CCCC)C2CC(C)(C)NC(C)(C)C2)n1)C1CC(C)(C)NC(C)(C)C1]

Educt 12 of the formula:

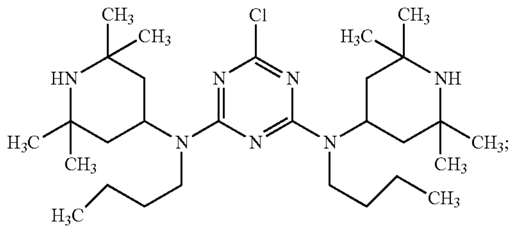 [SMILES: CCCCN(c1nc(Cl)nc(N(CCCC)C2CC(C)(C)NC(C)(C)C2)n1)C1CC(C)(C)NC(C)(C)C1]

Educt 13 of the formula:

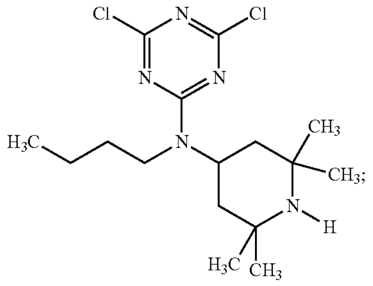 [SMILES: CCCCN(c1nc(Cl)nc(Cl)n1)C1CC(C)(C)NC(C)(C)C1]

Educt 14 of the formula:

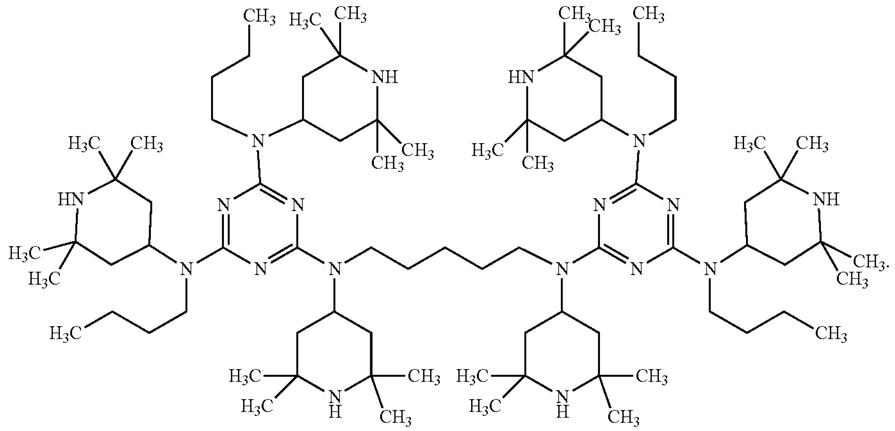 [SMILES: CCCCN(c1nc(N(CCCC)C2CC(C)(C)NC(C)(C)C2)nc(N(CCCCCN(c2nc(N(CCCC)C3CC(C)(C)NC(C)(C)C3)nc(N(CCCC)C3CC(C)(C)NC(C)(C)C3)n2)C2CC(C)(C)NC(C)(C)C2)C2CC(C)(C)NC(C)(C)C2)n1)C1CC(C)(C)NC(C)(C)C1]

Educt 15 of the formula:

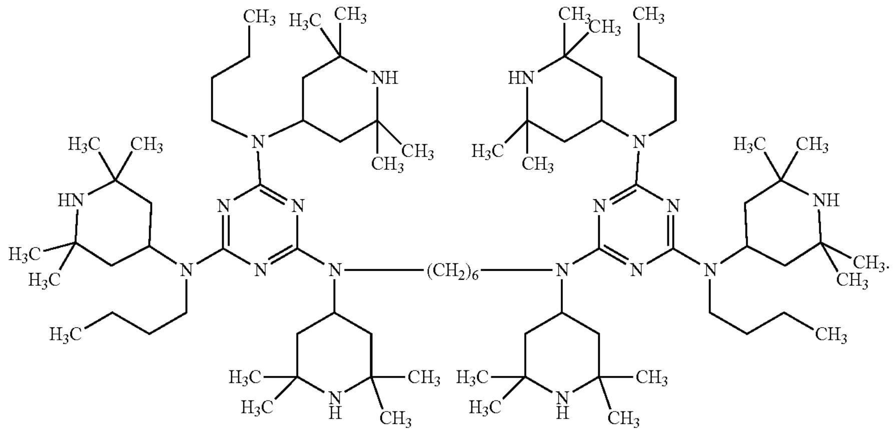

(which is the secondary amine analogue of examples 1-3 of WO2012-052377);

Educt 16 of the formula:

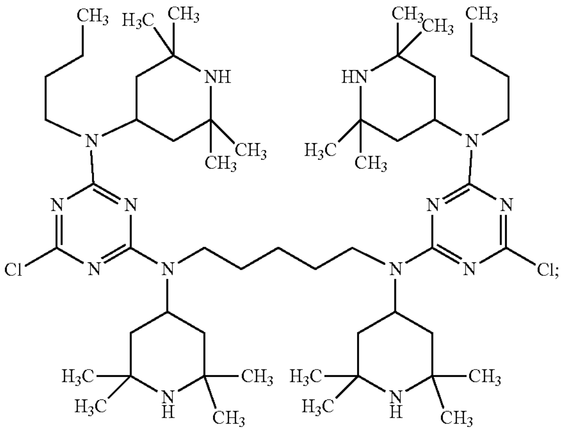 [SMILES: CCCCN(c1nc(Cl)nc(N(CCCCCN(c2nc(Cl)nc(N(CCCC)C3CC(C)(C)NC(C)(C)C3)n2)C2CC(C)(C)NC(C)(C)C2)C2CC(C)(C)NC(C)(C)C2)n1)C1CC(C)(C)NC(C)(C)C1]

Educt 17 of the formula:

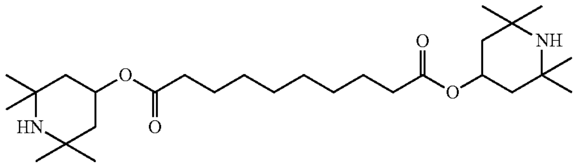

(bis(2,2,6,6-tetramethylpiperidin-4-yl)sebacate; available as Tinuvin 770 ® from BASF).

Educts 12, 13 and especially 16 are useful as an intermediate for oligomeric HALS and corresponding oligomeric N—O-alkyl HALS.

Nitroxyl compounds suitable as intermediates in the process of an embodiment of the invention include the compound of the formula

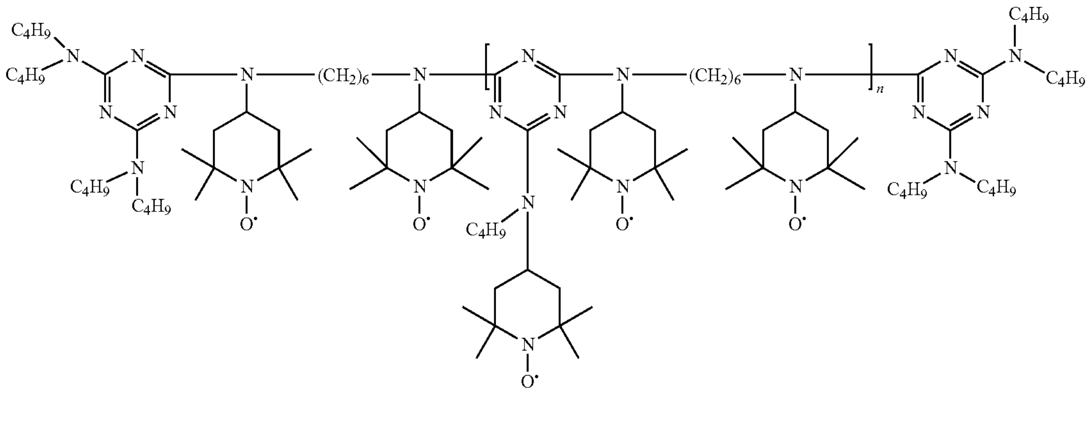

wherein n is from the range 1 to 10;

as well as any of the above secondary amine educts for present step (i) in oxidized form, as available as product of the present step (i).

Preferred products of the present process include the following compounds:

a) Bis(1-octyloxy-2,2,6,6-tetramethylpiperidin-4-yl)sebacate (i.e. Tinuvin 123 ®, CAS-No. 129757-67);

b) the product of CAS No. 191680-81-6 of the formula

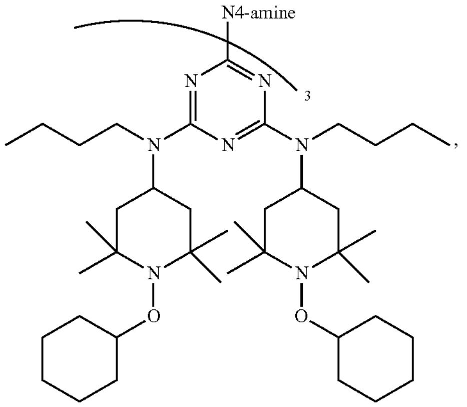

wherein N4-amine is a trivalent amine of the formula

XHN—$CH_2CH_2CH_2$—NX—$CH_2CH_2CH_2$—NX—$CH_2CH_2CH_2$—NHX (Xa), wherein 1 symbol X stands for hydrogen and 3 symbols X stand for a bond (Flamestab NOR 116 ®);

c)

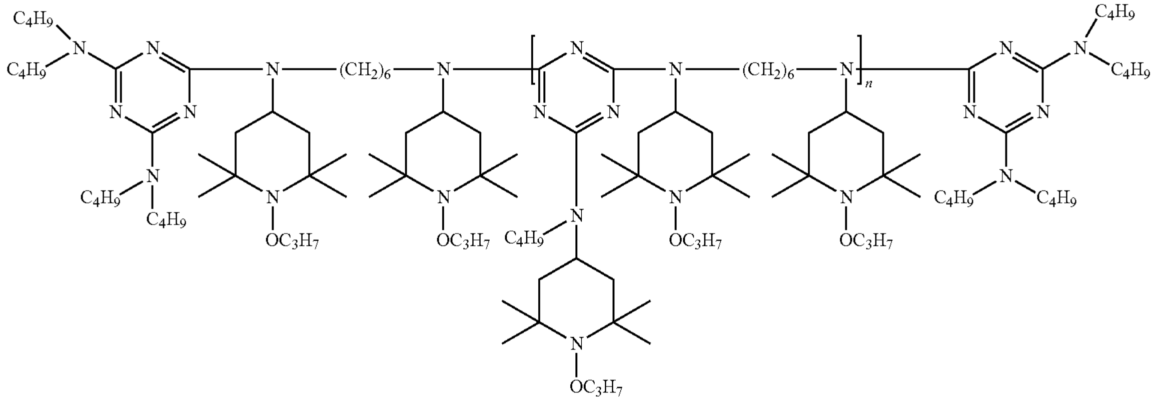

wherein n is a number from the range 1 to 10.

Also preferred as products of the present process are monomeric hindered amine ethers such as those of formula (XIV)

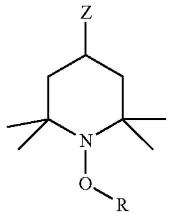

wherein R is as defined above and Z is hydrogen, OH or OR or OCOR or $N(R_1)R$ or oxo (i.e. O═);

some preferred oligomeric compounds obtainable in accordance with the process of an embodiment of the invention conform with the formula (XV)

(XV)

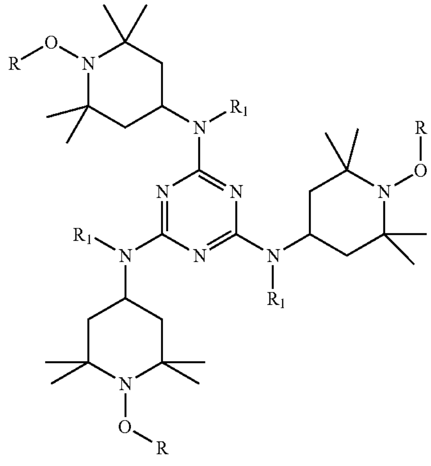

wherein R, $R_1$ are as defined above, and wherein R is preferably n-propyl or n-octyl or n-undecyl, and/or $R_1$ is preferably n-butyl;

as well as N—O-alkyl HALS compounds (a) and (b) above.

Sterically hindered alkoxyamine compounds, e.g. of the formula (I), which are obtainable in the present process, especially compounds containing moieties of the formula (Ia), such as the above compound of the formula (XV) or compounds a) to d), are effective stabilizers for organic materials such as organic polymers against the detrimental effects of light, oxygen and/or heat. Organic polymers, which may be stabilized in this way, are for example those listed in GB-A-2334717 from page 30, $10^{th}$ line from bottom, until page 35 line 9 from bottom; typical compositions of embodiments of the present invention are analogous to those described subsequently in this document from page 35 line 8 from bottom until page 36 replacing the HALS compound featured in GB-A-2334717 with the present sterically hindered alkoxyamine or one of the products of the below examples. Corresponding compositions may be thermoplastic polymer compositions, or may be coating compositions analogous to those described in GB-A-2334717 on pages 48 to page 54 line 19, which comprise one or more organic polymers. The compositions typically further contain coadditives such as disclosed in GB-A-2334717, pages 37 to 47.

As noted above, compound mixtures as presently obtainable and containing functionalities of formula (Ia) are advantageously usable as stabilizers for organic material, such as organic polymer compositions, against degradation by light, oxygen and/or heat. Products of the present process may also show an improved thermal stability compared to corresponding compositions or compounds prepared according to prior art processes as well as an improved antioxidant performance, especially during polymer processing conditions, preventing the degradation or oxidation of polymers during high temperature processing (e.g. extrusion, molding, etc).

The examples below further illustrate embodiments of the invention. All parts or percentages, in the examples as in the remainder of the description and in the claims, are by weight, unless stated otherwise. Room temperature denotes a temperature from the range 20-30° C. Overnight denotes a time period of at least 12 hours and up to 16 hours. Wherever mentioned, lower alkyl stands for $C_1$-$C_8$alkyl, especially $C_1$-$C_6$alkyl, such as methyl, ethyl, propyl, butyl, pentyl, hexyl. All peroxides (educt of formula A according to present process, such as di-butanoyl peroxide) are obtained in analogy to R. F. Drury and Z, L. Kaplan, Journal of the American Chemical Society, 94:11, May 31, 1972. The alkylation rate (NO-alkyl content) is determined from proton NMR as shown in Table 1, if not indicated otherwise. Within the formulae given, Bu as well as $C_4H_9$ each stands for 1-butyl. The index n used in formulas denotes a number of repetition, typically at least 3, for example 3 to 1000, if not defined otherwise.

Abbreviations

HPLC high pressure liquid chromatography
T temperature (given in ° C. if not otherwise indicated)
® registered trade mark
1H NMR proton nuclear magnetic resonance
MTBE methyl tert.-butyl ether
TMP tetramethyl piperidine Example 1 (Prior Art): Oxidation of Educt 2 (Chimassorb® 2020; from Org. Process Res. Dev. 2014, 18, 1843-1849)

A solution of Na2CO3·10H2O (1,08 g, 3.77 mmol) and Na2WO4·2H2O (0.93 g, 2.82 mmol) in deionized water (13 g) is added to a solution of Educt 2 (commercial product by BASF) (324 g, approximately 108 mmol) in toluene (486 g) at ambient temperature. Then, 50% H2O2 (308 g, 4.52 mol) is charged through a pump into the reaction mixture over 8 h while maintaining the temperature at 60° C. Next, 25% aqueous Na2CO3 (97 g) is dosed in over 0.5 h, and stirring is continued at 60° C. for 1 h. After phase separation at 70° C. and removal of the aqueous phase, the organic phase is washed with 23% NaCl (75 g). The aqueous phase is split-off and a reddish organic phase (709 g) is obtained. Pure product is obtained by removal of the organic solvent in vacuo as a red powder (see also Tab. 2).

Example 2: Conversion of the Intermediate Obtained in Example 1 (Educt 1) into an Alkoxyamine Ether a) 4.32 g of the intermediate of example 1 is dissolved in 30 ml of chlorobenzene. 2.66 g of dibutanoyl peroxide is added in small portions while heating the reaction mass to 90° C. The temperature is kept between 9° and 100° C. for 75 min. Upon cooling, 2 ml of water are added, stirring is continued for 30 mins, and then all volatile components are removed in vacuo at up to 90° C. The alkoxyamine content is determined by 1H NMR.
b) A mixture of 2.9 g of the intermediate of example 1 in toluene (80 ml) is heated slowly to 80° C. under stirring. Starting at 40° C., 2.4 g of dibutanoyl peroxide is added in 5 portions over a period of 60 min. Stirring is continued for 120 min. to provide a yellow/orange solution. Upon cooling, 5 ml of water are added, stirring is continued for 30 mins, and then all volatile components are removed in vacuo. The alkoxyamine content is determined by 1H NMR to be 95%.
c) A mixture of 0.65 g of the intermediate of example 1 in toluene (5 ml) is heated slowly to 90° C. under stirring. Starting at 40° C., 1.3 g of dilauroyl peroxide is added in portions over a period of 60 min. Stirring is continued for 120 min. to provide a yellow solution.

Upon cooling, all volatile components are removed in vacuo. The alkoxyamine content is determined by 1H NMR to be 95%.

Example 3: Improvement of the Color of Commercial Tinuvin® NOR® 371 (Available from BASF)

5.0 g of Tinuvin® NOR® 371 is dissolved in 20 ml of toluene. The mixture is heated to 85° C. under intense stirring. Dibutanoyl peroxide (2.1 g) is added in small portions to the reaction mixture over a period of 6 hours. Then, stirring is continued for another 8 hours. Upon cooling, all volatiles are removed in vacuo to provide a pale yellow foam. Removal of the initial color is apparent from UV/VIS measurements shown in Tab. 2.

Example 4: Improvement of the Alkoxyamine Content of Commercial Tinuvin® NOR® 371

0.5 g of Tinuvin® NOR® 371 is dissolved in 5 ml of toluene. Dibutanoyl peroxide (0.25 g) is added to the reaction mixture at ambient temperature. The mixture is heated to 50° C. until the red color disappears. Then, 2 ml of water are added dropwise and stirring is continued for 0.5 hours. Upon cooling, all volatiles are removed in vacuo to provide the optimized product. The alkoxyamine content is determined by 1H NMR to be 99%.

Example 5: Improvement of the Color and Alkoxyamine Content of Commercial Tinuvin® NOR®356 (Available from BASF)

0.5 g of commercially obtained Tinuvin® NOR®356 (educt) is dissolved in 5 ml of toluene. Dibutanoyl peroxide (0.25 g) is added to the reaction mixture at ambient temperature. The mixture is heated to 50° C. until the red color disappears. Then, 2 ml of water are added dropwise and stirring is continued for 0.5 hours. Upon cooling, all volatiles are removed in vacuo to provide a pale yellow foam. From the total amount of reactive nitrogen moieties which are convertible into alkoxyamine, 96% are converted as determined by 1H-NMR. Visual comparison shows that the reddish coloring of the educt has largely disappeared in the product as also shown in Tab. 2.

Example 6: General Procedure for the Preparation of Tert-Butyl Peroxy Esters (not Part of the Invention)

Under a nitrogen atmosphere, a 100 mL 3-neck flask, equipped with a magnetic stirring, a condenser, a thermometer and an addition funnel, and cooled with an ice-water bath, is charged with 25 ml of MTBE, 4.1 ml (22 mmoles) of 5.5 M tert-butylhydro-peroxide in decane and 2.5 ml (30.0 mmoles) of pyridine. The stirred mixture is cooled to 0° C. Over a period of 10-15 minutes, a solution of the desired acid chloride is slowly added (e.g. acetyl chloride, oxalyl chloride; 22 mmol for mono-functional acid chlorides; 11.0 mmoles for oxalic acid dichloride; dissolved in 5 ml of MTBE, respectively). Pyridinium chloride forms as a solid shortly after the addition commences. After the addition, the reaction mass is stirred for 60 minutes at 2° C. Then 10 mL of water are added and the reaction mass is stirred an additional 10 minutes at 3 to 4° C. The aqueous layer is then separated and the organic layer washed three times with 35 mL of aqueous 5% HCl solution and then twice with 75 mL portions of water. The product solution is dried over 5% by weight of anhydrous MgSO4, and, after separation of the desiccant by filtration, stored in a fridge at 4° C.

Example 7 (Embodiment of the Invention): Conversion of the Product of Example 1

With Products of Example 6 a) 3.0 ml of tert-butyl peroxyacetate (50 wt. % solution in aliphatic hydrocarbons) is diluted with 3.0 ml of xylenes. A solution of 2.8 g of product of example 1 in xylenes is added over the course of 45 mins at 132-138° C. After 2 hours of additional stirring a pale yellow solution is obtained. All volatiles are removed in vacuo at 90° C. to yield an off-white foam, 2.47 g. The alkoxyamine content is determined by 1H NMR to be 84%.
b) A solution of di-t-butylperoxy-oxalate in toluene is heated to 60-70° C. A solution of product of example 0.1 in toluene is added over the course of 30 mins. After 2 hours of additional stirring a pale yellow solution is obtained. All volatiles are removed in vacuo to yield an off-white foam. The presence of alkoxyamine is determined by proton NMR (signal at 3.74 ppm).

Example 8 (not Part of Present Invention)

a) Preparation of Educt Compound 1 of the Formula (Educt 1)

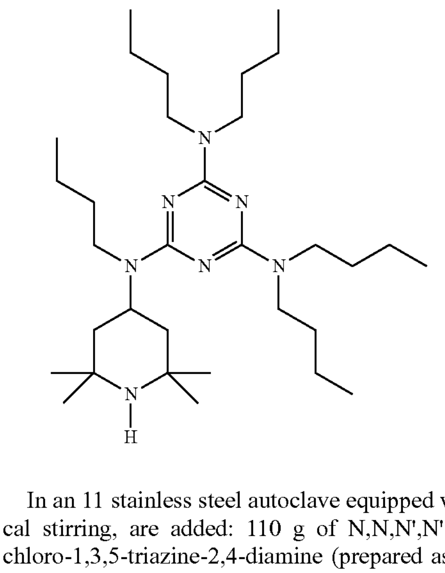

In an 11 stainless steel autoclave equipped with mechanical stirring, are added: 110 g of N,N,N',N'-Tetrabutyl-6-chloro-1,3,5-triazine-2,4-diamine (prepared as described in Katritzky, Alan R.; Oniciu, Daniela C.; Ghiviriga, Ion; Barcock, Richard A. Journal of the Chemical Society, Perkin Transactions 2: Physical Organic Chemistry (1972-1999), 1995, #4 p. 785) dissolved in 300 ml of xylene, 64 g of 2,2,6,6-Tetramethyl-4-n-butylamino-piperidine (nBut-TAD, commercially available from Evonik or other suppliers), then 43 ml of 30% aqueous NaOH. The autoclave is then closed, put under vigorous stirring and heated to 180° C. and left to react for 12 hours.

The reaction mixture is left to cool down to 50° C., the water phase is discarded, the organic phase washed a few times with deionized water under vigorous stirring, until the aqueos phase is neutral in pH.

The organic phase is then transferred to the rotavap, all solvent is removed under vacuum to obtain an off white solid, which is dried overnight in a vacuum oven.

The final product (Educt 1, MW 567, white powder) is weighted to calculate the yield and characterized via NMR.

Example 9: Preparation and Selective Alkylation of the Compound 2 of the Formula (Compoud 2)

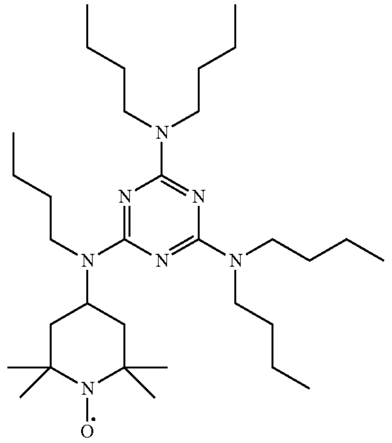

In a 350 ml round bottom flask, equipped with mechanical stirrer, reflux condenser, thermometer, addition funnel, are introduced at room temperature: 100 ml of toluene, 100 ml of tert·Butanol, 25 g of Compound 1 and 9 g of $NaHCO_3$ dissolved in 120 ml of deionized water. The reaction mixture is heated to 50° C.

From the dropping funnel, 19.5 g of 35% peracetic acid are introduced dropwise, keeping the temperature below 60° C. Then the reaction mixture is cooled to 20° C., transferred to a separation funnel, the water phase is discarded. The organic phase is then washed a few times with water until neutral pH.

At this point, about 0.5 ml of di-butanoyl peroxide (prepared according to R. F. Drury and Z, L. Kaplan, Journal of the American Chemical Society, 94:11, May 31, 1972) of the formula

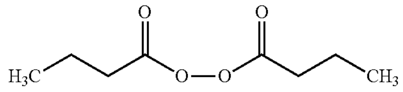

(MW 174) are added to the reaction mixture, heated to 80° C. and left to react overnight. At the end of the reaction, the mixture is washed with an aqueous solution of sodium sulphite, then concentrated in the rotavap to remove the solvent and all volatile products. The final product of the formula

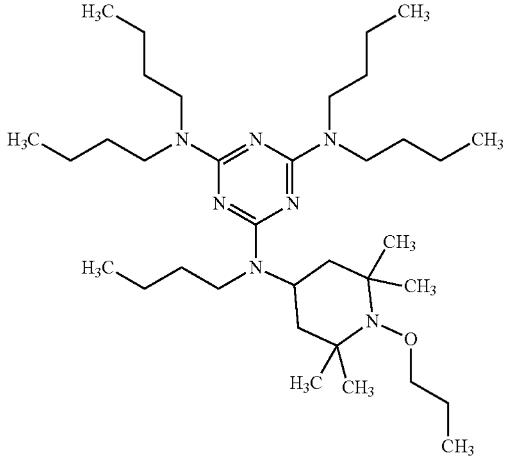 [SMILES: CCCCN(CCCC)c1nc(N(CCCC)CCCC)nc(N(CCCC)C2CC(C)(C)N(OCCC)C(C)(C)C2)n1]

is characterized by HPLC and 1H-NMR.

$^1$H-NMR ($CDCl_3$), δ (ppm) 0.83-1.08 (m, 30H), 1.26-1.40 (m, 10H), 1.44-1.64 (m, 14H), 1.73 (qt, 2H), 3.20-3.35 (m, 10H), 3.43 (m, 1H), 3.71 (t, 2H).

HPLC (Waters Alliance 2690/2695 HPLC System with Waters 2996 PDA Detector, column Hypersil GOLD™ C4x5 cm; Method: isocratic 95/5 $CH_3CN/H_2O$, temperature 70° C., 1.0 ml/min, UV detector at 240 nm) shows a residual peak of the starting materials of 2% and a 95% peak for the desired product.

Example 10: Reaction of the Di-Lauroyl Peroxide with Compound 2

The procedure described in example 2 is repeated except that di-butanoyl peroxide is replaced by di-1-dodecanoic peroxide. The product 2-(1-undecanoxy-2,2,6,6-tetramethylpiperidine-4-yl)-butylamino-4,6-bis(dibutylamino)-1,3,5-triazine is characterized by HPLC and $^1$H-NMR.

The superior quality of products of the present process are also apparent from the following tables. Table 1 compiles data obtained by 1H-NMR for the alkylation rate of the nitroxyl intermediate; Table 2 shows data indicating the colour of certain products by UV/Vis measurement of the absorption at 470 nm (absorption maximum of the nitroxide radical in solution).

TABLE 1

Rate of alkylation of the nitroxyl intermediate as detected by 1H-NMR

| | Tinuvin ® NOR ® 371 (BASF) | Product of example 4 | Tinuvin ® NOR ® 356 (BASF) | Product of example 5 |
|---|---|---|---|---|
| NO—CH2—CH2—CH3 signal integral *) | 1.56 | 1.97 | | |
| NO—CH2—CH2—CH3 to reference ratio *) | | | 1.44 | 1.71 |
| NO-alkyl content | 78% | 99% | 71% | 96% **) |

*) Reference signal: proton in 4 position of TMP ring (1 H)

**) Based on amount of educt nitroxide groups

TABLE 2

| Absorption at 470 nm, comparison by UV/Vis measurement | | |
|---|---|---|
| Sample | Absorption at 470 nm *) | Concentration |
| Product of example 1 | 0.706 | 0.1 g in 5.0 ml toluene |
| Tinuvin ® NOR ® 371 (BASF) | 0.329 | 0.1 g in 3.0 ml toluene |
| Product of example 3 | 0.178 | 0.1 g in 3.0 ml toluene |
| Product of example 2b | 0.217 | 0.1 g in 3.0 ml toluene |
| Tinuvin ® NOR ® 356 (BASF) | 0.145 | 0.1 g in 5.0 ml toluene |
| Product of example 5 | 0.079 | 0.2 g in 2.0 ml toluene |
| Product of example 7a | 0.135 | 0.2 g in 2.0 ml toluene |

*) maximum of absorption of nitroxide radical in solution

Treatment in accordance with the present process results in a less colored product with clearly improved alkylation rate.

While subject matter of the present disclosure has been illustrated and described in detail in the drawings and foregoing description, such illustration and description are to be considered illustrative or exemplary and not restrictive. Any statement made herein characterizing the invention is also to be considered illustrative or exemplary and not restrictive as the invention is defined by the claims. It will be understood that changes and modifications may be made, by those of ordinary skill in the art, within the scope of the following claims, which may include any combination of features from different embodiments described above.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A process for alkylating a sterically hindered nitroxyl compound to the corresponding sterically hindered alkoxyamine, which process comprises reacting the sterically hindered nitroxyl compound with a peroxide selected from diacyl peroxides of the formula (A), peresters of the formula (A) and oxalic acid peresters of the formula (D)

R—CO—O—O—Z—R (A),

R—Z"—X—CO—CO—O—O—Z"—R (D), wherein each R independently stands for a primary or secondary alkyl or cycloalkyl radical and X is oxygen —O— or a peroxy group —O—O—, Z stands for CO or an alkylene bonded over a quaternary carbon atom, which is an alkylene of the formula (C)

R'—C—R' (C)

wherein each R' is selected from alkyl of 1 to 15 carbon atoms,

Z" stands for the alkylene bonded over a quaternary carbon atom of the formula (C), provided that, in case that Z is CO, the sterically hindered nitroxyl compound is not 4-hydroxy-1-oxyl-2,2,6,6-tetramethyl-piperidine.

2. A process for alkylating a sterically hindered nitroxyl compound to the corresponding sterically hindered alkoxyamine according to claim 1, which process comprises reacting the sterically hindered nitroxyl compound with a peroxide of the formula (A)

R—CO—O—O—Z—R (A), wherein each R independently stands for a primary or secondary alkyl or cycloalkyl radical, the primary or secondary alkyl or cycloalkyl radical, and Z stands for CO or an alkylene bonded over a quaternary carbon atom, which is an alkylene of the formula (C)

R'—C—R' (C)

wherein each R' is selected from alkyl of 1 to 15 carbon atoms, provided that, in case that Z is CO, the sterically hindered nitroxyl compound is not 4-hydroxy-1-oxyl-2,2,6,6-tetramethyl-piperidine.

3. The process of claim 1, wherein the peroxide is of the formula (A)

and is a di-acylperoxide and Z stands for CO, or is a perester and Z stands for an alkylene bonded over a quaternary carbon atom of the formula (C), or wherein the peroxide is an oxalic acid perester of the formula (D)

and in which process:

the sterically hindered nitroxyl compound comprises one or more moieties 1-oxyl-2,2,6,6-tetramethyl-piperidine of the formula (IIIa), wherein the asterisk indicates the location of the bond linking these moieties to another part of the molecule (IIIa)

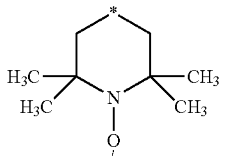

and the corresponding sterically hindered alkoxyamine compound belongs to the class of 1-alkoxy-2,2,6,6-tetramethyl-piperidines containing one or more moieties of the formula (Ia), wherein the asterisk indicates the location of the bond linking these moieties to another part of the molecule (Ia)

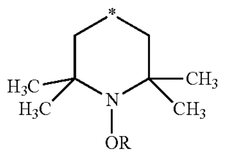

wherein R is a primary or secondary alkyl or cycloalkyl radical.

4. The process according to claim 3, wherein the sterically hindered alkoxyamine compound conforms to the formula (Ib)

$$(HA)_pY \quad (Ib)$$

wherein
HA is a hindered amine ether moiety (HE) of the formula (Ia);
p is a number from the range 1 to 6,
and wherein
Y is an anchor group of valency 2 to 6 of the formula (IX)

$$T_3\text{-}(N[T_4]\text{-}A_2)_q\text{-}N[T_1T_2] \quad (IX)$$

wherein q ranges from 0 to 3,
or Y is an anchor group as further defined below;
when p is 1,
Y is an anchor group of the formula —$NR_1$-$A_1$;
when p is 2, Y is an anchor group of the formula DC-$A_2$-DC;
or Y is the divalent anchor group of the formula (IX), wherein:
q is zero, $T_3$ stands for an open bond, $T_1$ is as defined for $R_1$ and $T_2$ is a divalent aminotriazinyl of the formula (X)

(X)

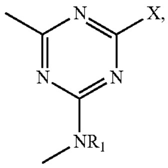

X, or q is 1, each of $T_1$ and $T_3$ is as defined for $R_1$ and each of $T_2$ and $T_4$ is the divalent aminotriazinyl of the formula (X);
when p is 3, Y is a trivalent anchor group of the formula (IX), wherein q is zero, $T_3$ stands for an open bond, $T_1$ is as defined for $R_1$ and $T_2$ is a trivalent diaminotriazinyl of the formula (XI)

(XI)

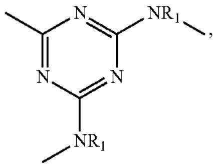

, or q is 1, $T_1$ is as defined for $R_1$, $T_2$ is a divalent aminotriazinyl of the formula (X), and $T_3$ and $T_4$ independently stand for an open bond or a divalent aminotriazinyl of the formula (X);
when p is 4, Y is a tetravalent anchor group of the formula (IX), wherein q is 3 and $T_2$ and two of the residues $T_4$ stand for a divalent diaminotriazinyl of the formula (XI), while each $T_1$ and $T_3$ and the remaining residue $T_4$ are as defined for $R_1$;
when p is 5, Y is a pentavalent anchor group of the formula (IX), wherein q is 1, $T_1$ is a trivalent diaminotriazinyl of the formula (XI), $T_3$ is a divalent aminotriazinyl of the formula (X), and $T_2$ and $T_4$ independently stand for an open bond or a divalent aminotriazinyl of the formula (X);

when p is 6, Y is a hexavalent anchor group of the formula (IX), wherein
q is 1, each of $T_1$ and $T_3$ is a trivalent diaminotriazinyl of the formula (XI), and $T_2$ and $T_4$ independently stand for an open bond or a divalent aminotriazinyl of the formula (X);
or q is 2 and $T_2$ and each $T_4$ stand for a trivalent diaminotriazinyl of the formula (XI), while each $T_1$ and $T_3$ is as defined for $R_1$;
or q is 3 and $T_2$ and two of the residues $T_4$ stand for a trivalent diaminotriazinyl of the formula (XI), while each $T_1$ and $T_3$ and the remaining residue $T_4$ are as defined for $R_1$;
or q is 3 and $T_2$ and $T_3$ and one of the residues $T_4$ stand for a trivalent diaminotriazinyl of the formula (XI), while each $T_1$ and the remaining residue $T_4$ are as defined for $R_1$;
$A_1$ is $C_1$-$C_{12}$alkyl or $C_2$-$C_{12}$alkyl interrupted by O or COO;
$A_2$ is $C_2$-$C_{12}$alkylene;
DC is a divalent connecting moiety; and
$R_1$ is H or lower alkyl; and
X is Cl or $N(R_1)_2$;
or the sterically hindered nitroxyl compound is an oligomeric or polymeric compound comprising 6 or more moieties of the formula (Ia) and/or (IIIa), where at least one moiety of the formula (IIIa) is present.

5. The process of claim 1, wherein R in formula (A) or (D) is independently selected from methyl, ethyl, 1-propyl, 2-propyl, 1-butyl, 2-butyl, 1-pentyl, 2-pentyl, 3-pentyl, 1-hexyl, 2-hexyl, 3-hexyl, 1-heptyl, 2-heptyl, 3-heptyl, 4-heptyl, 1-octyl, 2-octyl, 3-octyl, 4-octyl, nonyl, decyl, undecyl, dodecyl, cyclopentyl, cyclohexyl, cycloheptyl, cyclooctyl, cyclononyl, cyclodecyl, cycloundecyl, and cyclododecyl.

6. The process of claim 1, wherein the reaction is carried out at a temperature from the range 0 to 140° C.

7. The process according to claim 1, wherein the peroxide is a diacyl peroxide of the formula (A) or a oxalic acid perester of the formula (D) and the reaction is carried out at a temperature from the range 15 to 100° C.; or the peroxide is a perester of the formula (A) and the reaction is carried out at a temperature from the range 30 to 140° C.

8. The process according to claim 1, wherein the reaction is carried out for a period of 5 minutes to 100 hours and/or the reaction is carried out in the absence of a heavy metal catalyst and/or wherein the reaction is carried out under a protective gas excluding oxygen.

9. The process according to claim 1, wherein the reaction is carried out in the presence of a solvent, which is selected from non-polar solvents polar solvents, and mixtures of non-polar and polar solvents.

10. The process according to claim 3, wherein the sterically hindered alkoxyamine obtained in the process is a compound of the formula (I)

$$(R_2)_2N\text{—}OR \quad (I)$$

wherein R is a primary or secondary alkyl or cycloalkyl radical, and
each $R_2$ is a hydrocarbon, both $R_2$ together containing 2 to 500 carbon atoms.

11. The process according to claim 1 for the preparation of a sterically hindered alkoxyamine compound, which conforms to the formula (XIV) or (XV)

(XIV)

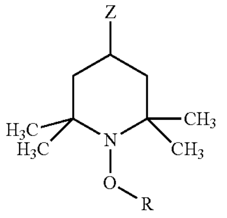

(XV)

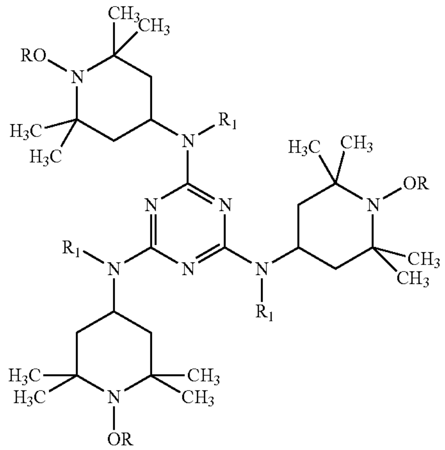

wherein R is a primary or secondary alkyl or cycloalkyl radical, $R_1$ is defined as H or lower alkyl, and Z is hydrogen or OR or OCOR or $N(R_1)R$ or oxo;

or is bis(1-octyloxy-2,2,6,6-tetramethylpiperidin-4-yl)sebacate;

or is an oligomeric or polymeric compound comprising at least 6 moieties if the formula (Ia) wherein the asterisk indicates the location of the bond linking these moieties to another part of the molecule (Ia)

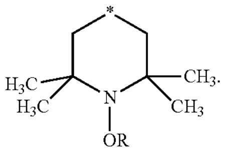

12. The process according to claim 1, wherein the sterically hindered nitroxyl compound is represented by one of the formulae (IV) or (V)

(IV)

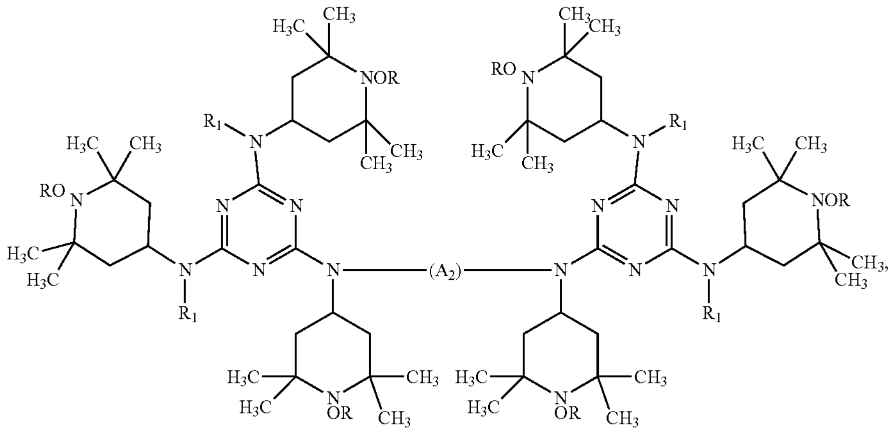

wherein $A_2$ is $C_2$-$C_{12}$alkylene;

$R_1$ is H or lower alkyl; and

R is a primary or secondary alkyl or cycloalkyl radical;

(V)

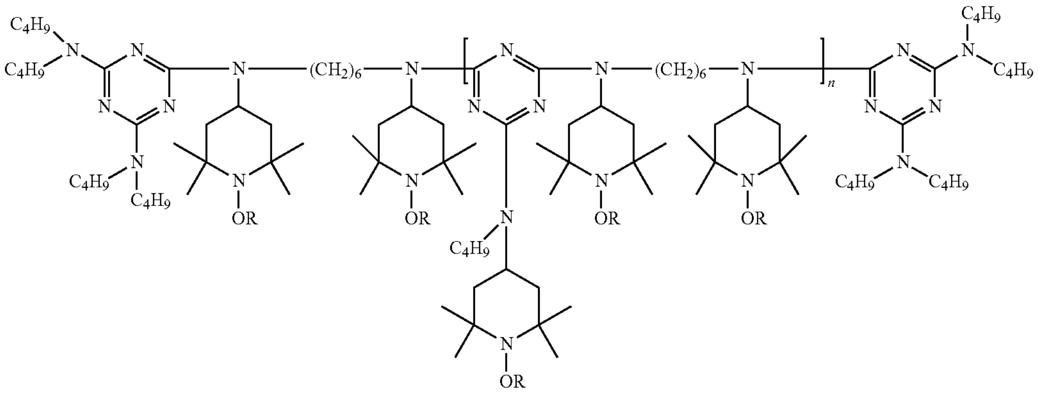

wherein n is from the range 1 to 10 and R is a primary or secondary alkyl or cycloalkyl radical;

or is represented by the formula

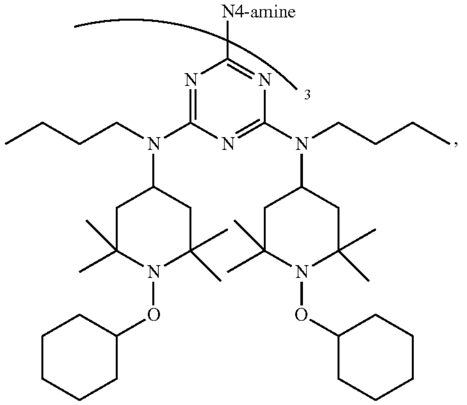

wherein N4-amine is a trivalent amine of the formula $XHN—CH_2CH_2CH_2—NX—CH_2CH_2CH_2—NX—CH_2CH_2CH_2—NHX$, wherein 1 symbol X stands for hydrogen and 3 symbols X stand for a bond;

and wherein one or more of the residues O—R is replaced by nitroxyl.

13. The process according to claim 1, wherein, in a first step (i), a sterically hindered secondary amine educt is converted into the sterically hindered nitroxyl compound, the process comprising:

(i) contacting the secondary hindered amine educt with a suitable oxidant to obtain a nitroxide (NO); and subsequently (ii) reacting the product obtained in step (i) with a peroxide.

14. The process according to claim 12, wherein the peroxide is of formula (A) or (B) and the sterically hindered alkoxyamine product conforms to the formula (V).

15. An oligomeric or polymeric product comprising compounds containing at least 6 moieties of the formula (Ia), wherein the asterisk indicates the location of the bond linking these moieties to another part of the molecule, (Ia)

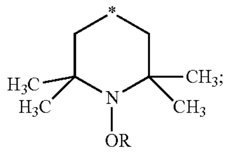

corresponding to one of the formulae (IV) or (V)

(VI)

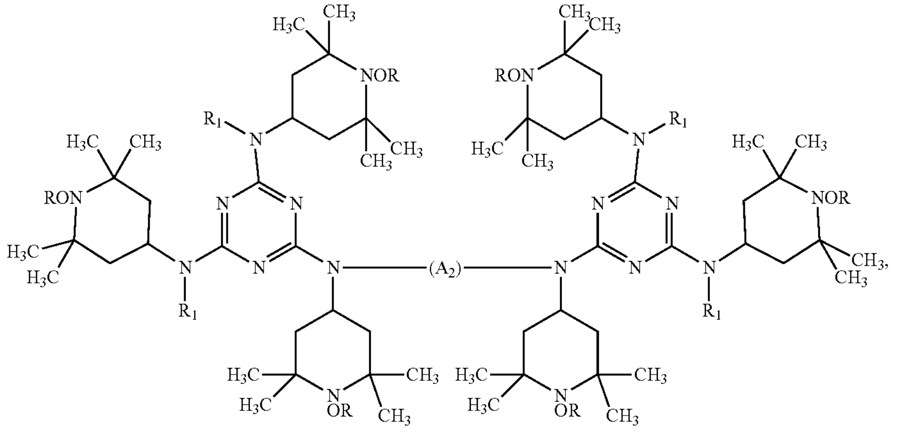

wherein $A_2$ is $C_2$-$C_{12}$alkylene and $R_1$ is H or lower alkyl and R is as defined below for formula (V), (V)

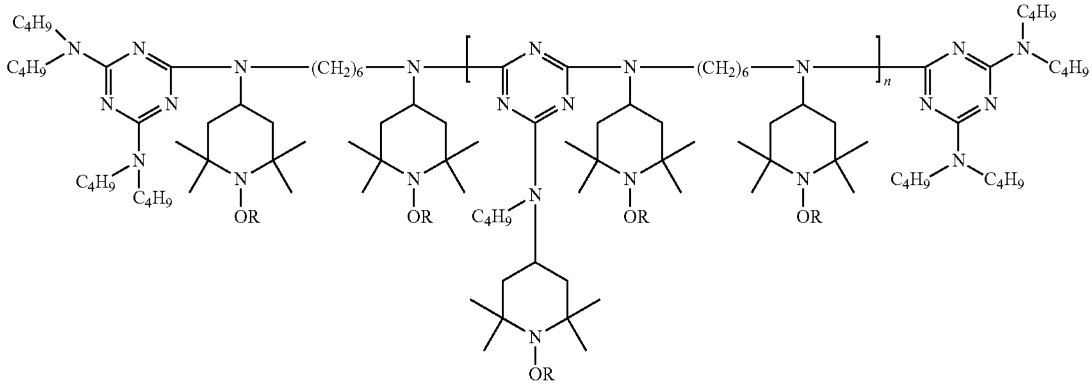

wherein n ranges from 1 to 10, and R is a primary or secondary alkyl or cycloalkyl radical;

wherein the oligomeric or polymeric product is obtained by the process according to claim 1, wherein the oligomeric or polymeric product represented by formula (V) contains more than 87% of N—O moieties in alkylated form as N—OR, wherein R is $C_1$-$C_5$ alkyl.

16. An oligomeric or polymeric product comprising compounds containing at least 6 moieties of the formula (Ia), wherein the asterisk indicates the location of the bond linking these moieties to another part of the molecule, (Ia)

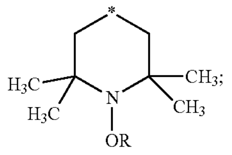

corresponding to formula (V)

(V)

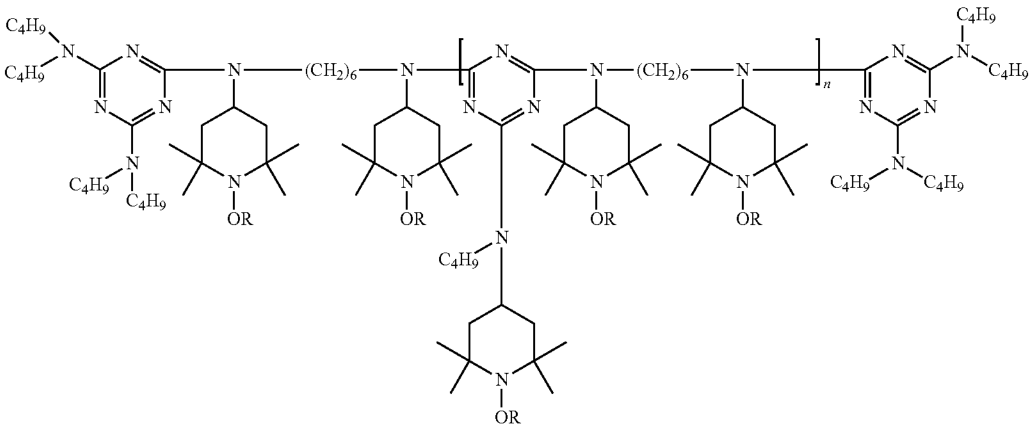

wherein n ranges from 1 to 10, and R is a primary or secondary alkyl or cycloalkyl radical, wherein the product contains more than 87% of N—O moieties in alkylated form as N—OR, wherein R is $C_1$-$C_5$ alkyl.

17. The process of claim 2, wherein the peroxide is of the formula (A)

and is a di-acylperoxide and Z stands for CO, or is a perester and Z stands for an alkylene bonded over a quaternary carbon atom of the formula (C); or wherein the peroxide is an oxalic acid perester of the formula (D)

and in which process:

the sterically hindered nitroxyl compound comprises one or more moieties 1-oxyl-2,2,6,6-tetramethyl-piperidine of the formula (IIIa), wherein the asterisk indicates the location of the bond linking these moieties to another part of the molecule (IIIa)

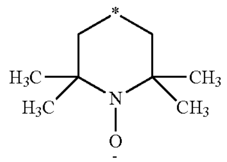

and the corresponding sterically hindered alkoxyamine compound belongs to the class of 1-alkoxy-2,2,6,6-tetramethyl-piperidines containing one or more moieties of the formula (Ia), wherein the asterisk indicates the location of the bond linking these moieties to another part of the molecule (Ia)

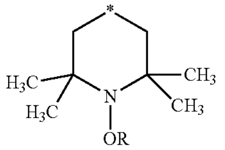

wherein R is a primary or secondary alkyl or cycloalkyl radical.

18. The process of claim 6, wherein the reaction is carried out at a temperature from the range 0 to 120° C., and in the presence of an inert solvent.

19. The process of claim 13, and wherein the secondary amine educt is an oligomeric or polymeric compound comprising at least 6 2,2,6,6-tetramethyl-piperidin-4-yl moieties, selected from the following:

Educt 2 of the formula:

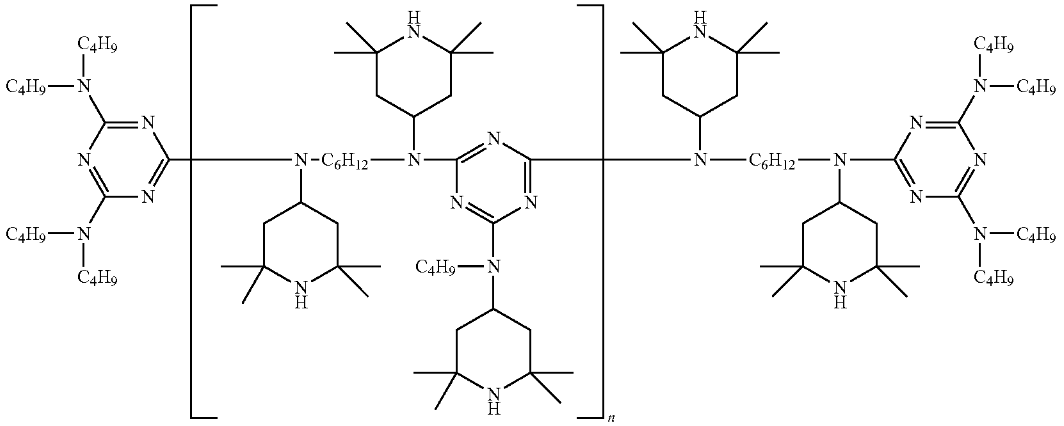

wherein n is from the range 1110;

Educt 3 of the formula:

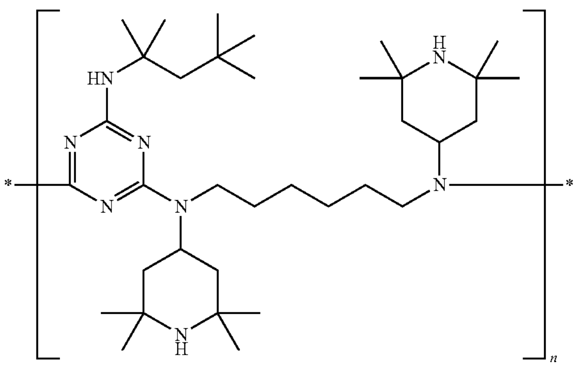

wherein n ranges from 1 to 10;
Educt 5 of the formula:
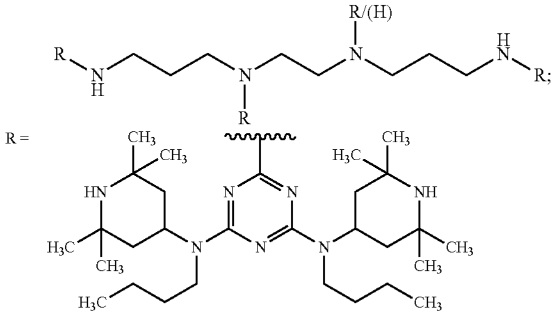
Educt 15 of the formula:
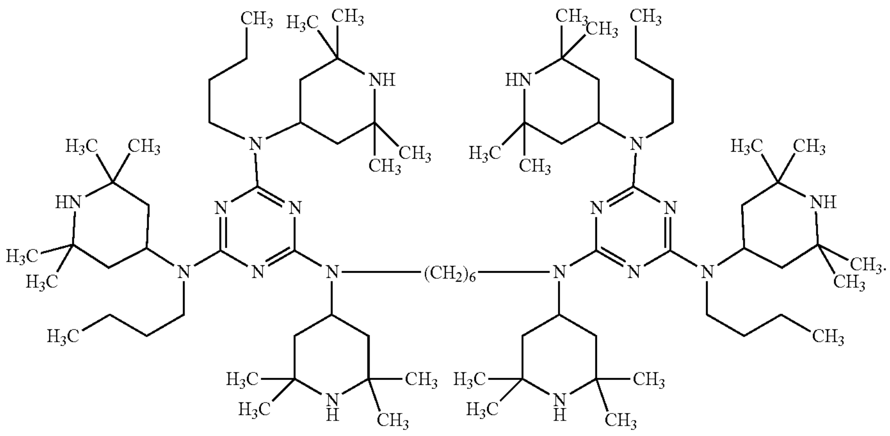
* * * * *